United States Patent [19]
Cleland et al.

[11] Patent Number: 6,080,429
[45] Date of Patent: *Jun. 27, 2000

[54] METHOD FOR DRYING MICROSPHERES

[75] Inventors: Jeffrey L. Cleland, San Carlos; Andrew J. S. Jones, San Mateo; Michael Frank Powell, San Francisco, all of Calif.

[73] Assignee: Genentech, Inc., South San Francisco, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/966,850

[22] Filed: Nov. 7, 1997

Related U.S. Application Data

[63] Continuation of application No. 08/650,364, May 20, 1996, abandoned, which is a continuation of application No. 08/143,313, Oct. 25, 1993, abandoned.

[51] Int. Cl.[7] .............................. A61K 9/50; B01J 13/04
[52] U.S. Cl. .................... 424/489; 424/486; 424/497; 264/4.1; 264/4.3; 427/2.15; 427/213.32; 427/213.36; 514/963; 514/965
[58] Field of Search .......................... 264/4.1, 4.3, 4.6; 427/2.15, 213.32, 213.36; 424/486, 497, 489; 514/963, 965

[56] References Cited

U.S. PATENT DOCUMENTS

| | | | |
|---|---|---|---|
| 3,565,559 | 2/1971 | Sato et al. | 264/4.3 X |
| 3,737,337 | 6/1973 | Schnoring et al. | 264/4.6 X |
| 4,293,539 | 10/1981 | Ludwig et al. | |
| 4,389,330 | 6/1983 | Tice et al. | 427/213.36 |
| 4,524,067 | 6/1985 | Arichi et al. | 514/33 |
| 4,568,559 | 2/1986 | Nuwayser et al. | 427/2.15 |
| 4,637,905 | 1/1987 | Gardner | 264/4.3 |
| 4,652,441 | 3/1987 | Okada et al. | 424/497 |
| 4,675,189 | 6/1987 | Kent et al. | 424/497 X |
| 4,719,246 | 1/1988 | Murdoch et al. | 521/134 |
| 4,728,721 | 3/1988 | Yamamoto et al. | 528/361 |
| 4,767,628 | 8/1988 | Hutchinson et al. | 424/426 |
| 4,849,228 | 7/1989 | Yamamoto et al. | 424/457 |
| 4,897,268 | 1/1990 | Tice et al. | 424/422 |
| 4,902,515 | 2/1990 | Loomis et al. | 424/486 |
| 4,917,893 | 4/1990 | Okada et al. | 424/423 |
| 4,954,298 | 9/1990 | Yamamoto et al. | 264/4.6 |
| 4,962,091 | 10/1990 | Eppstein et al. | 514/2 |
| 4,990,336 | 2/1991 | Silvestri et al. | 424/426 |
| 5,008,116 | 4/1991 | Cahn | 424/491 |
| 5,057,540 | 10/1991 | Kensil et al. | 514/25 |
| 5,068,112 | 11/1991 | Samejima et al. | 424/497 X |
| 5,075,109 | 12/1991 | Tice et al. | 424/499 X |
| 5,100,669 | 3/1992 | Hyon et al. | 427/213.36 X |
| 5,198,533 | 3/1993 | Schally et al. | 530/313 |
| 5,348,867 | 9/1994 | Georgiou et al. | 435/69.7 |
| 5,624,612 | 4/1997 | Sewall et al. | 264/4.1 |
| 5,667,808 | 9/1997 | Johnson et al. | 264/4.6 X |

FOREIGN PATENT DOCUMENTS

| | | |
|---|---|---|
| 7992987 | 4/1988 | Australia . |
| 266 119A2 | 5/1988 | European Pat. Off. . |
| 0 279 688 A2 | 8/1988 | European Pat. Off. . |
| 333523 A2 | 9/1989 | European Pat. Off. . |
| 442671 A2 | 8/1991 | European Pat. Off. . |
| WO 90/03984 | 4/1990 | WIPO . |
| WO 91/12882 | 9/1991 | WIPO . |
| WO 93/07861 | 4/1993 | WIPO . |

OTHER PUBLICATIONS

Wang et al., "Influence of formulation methods on the in vitro controlled release of protein from poly(ester) microspheres" *J. of Controlled Release* 17:23–32 (1991).

Watts et al., "Microencapsulation Using Emulsification/Solvent Evaporation: An Overview of Techniques and Applications" *Crit. Reviews in Therapeutic Drug Carrier Systems* 7(3):235–259 (1990).

Alonso et al., "Determinants of Release Rate of Tetanus Vaccine from Polyester Microspheres" *Pharm. Res.* 10(7):945–953 (1993).

Arthur et al., "Challenge of chimpanzees (Pan troglodytes) immunized with human immunodeficiency virus envelope glycoprotein gp120" *Journal of Virology* 63(12):5046–5053 (1989).

Berman et al., "Human immunodeficiency virus type 1 challenge of chimpanzees immunized with recombinant envelope glycoprotein gp120" *Proc. Natl. Acad. Sci. USA* 85(14):5200–5204 (Jul. 1988).

Chang et al., "Biodegradable Semipermeable Microcapsules Containing Enzymes, Hormone, Vaccines, and other Biologicals" *J. Bioengineering* 1:25–32 (1976).

Cohen, "Jitters Jeopardize AIDS Vaccine Trials" *Science* 262:980–981 (1993).

Cowsar et al., "Poly(lactide–co–glycolide) Microcapsules for Controlled Release of Steroids" *Methods in Enzymology* 112:101–116 (1985).

Eldridge et al., "Biodegradable and Biocompatible Poly (DL–Lactide–Co–Glycolide) Microspheres as an Adjuvant for Staphylococcal Enterotoxin B Toxoid Which Enhances the Level of Toxin–Neutralizing Antibodies" *Infection and Immunity* 59(9):2978–2986 (1991).

Eldridge et al., "Biodegradable Micropheres As a Vaccine Delivery System" *Molecular Immuno.* 28(3):287–294 (1991).

Eldridge et al., "Biodegradable Poly (DL–lactide–coglycolide) Microspheres" *Res. Immunol.* 143(5):557–563 (1992).

Glaser, V., "Solving the HIV Vaccine Puzzle: Questions Still Outnumber the Answers" *Genetic Engineering News* pp. 15–30 (Nov. 1, 1993).

(List continued on next page.)

*Primary Examiner*—Richard D. Lovering
*Attorney, Agent, or Firm*—McCutchen, Doyle, Brown, & Enersen, LLP; Emily M. Haliday

[57] ABSTRACT

A method for drying microspheres in a fluidized bed is provided, along with a composition comprising microspheres dried by that method.

24 Claims, 3 Drawing Sheets

OTHER PUBLICATIONS

Hu et al., "Effect of immunization with a vaccinia–HIV env recombinant on HIV infection of chimpanzees" *Nature* 328(6132):721–723 (Aug. 1987).

Jeffery et al., "The Preparation and Characterization of Poly(lactide–co–glycolide) Microparticles. II. The Entrapment of a Model Protein Using a (Water–in–Oil)–in Water Emulsion Solvent Evaporation Technique" *Pharm. Res.* 10(3):362–368 (Mar. 1993).

Kensil et al., "Development of a genetically engineered vaccine against feline leukemia virus infection" *J. Amer. Veterinary Med. Assoc.* 199(10):1423–1427 (1991).

Maulding, "Prolonged Delivery of Peptides by Microcapsules" *J. of Controlled Release* 6:167–176 (1987).

Nellore et al. [20~, "Evaluation of Biodegradable Microspheres as Vaccine Adjuvant for Hepatitis B Surface Antigen" *J. Parenteral Science & Technology* 46(5):176–180 (1992).

Newman et al., "Immunogenicity and Toxicity Testing of an Experimental HIV–1 Vaccine in Nonhuman Primates" *Aids Res. and Human. Retroviruses* 8(8):1413–1418 (1992).

Nunberg et al., "Adjuvant Formulations to Increase the Virus–neutralizing Antibody Response to HIV–1 rgp120 Subunit Vaccine" *Vaccines* (Annu. Meet.), Norrby et al., 11th edition, N.Y.:Cold Spring Harbor Lab vol. 94:23–27 (Mod. Approaches New 1994).

O'Hagan et al., "Biodegradable Microparticles as Controlled Release Antigen Delivery System" *Immunology* 73(2):239–242 (1991).

Putney, S., "How Antibodies Block HIV Infection: Paths to an AIDS Vaccine" *TIBS* 17:191–196 (1992).

Sanders et al., "Controlled Release of a Luteinizing Hormone–Releasing Hormone Analogue from Poly (d,l–lactide–co–glycolide) Microspheres" *J. of Pharmaceutical Sciences* 73(9):1294–1297 (1984).

Tabata et al., "Activation of Macrophage in Vitro to Acquire Antitumor Activity by a Muramyl Dipeptide Derivative Encapsulated in Microspheres Composed of Lactide Copolymer" *Journal of Controlled Release* 6:189–204 (1987).

White et al., "A purified Saponin Acts as an Adjuvant for a T–independent Antigen" *Immunobiology of Proteins and Peptides VI*, M.Z. Atassi, New York:Plenum Press pp. 207–210 (1991).

Wu et al., "Saponin Adjuvant Enhancement of Antigen–Specific Immune Responses To An Experimental HIV–1 Vaccine" *J. of Immuno.* 148(5):1519–1525 (1992).

METHOD FOR DRYING MICROSPHERES

This is a continuation of application(s) Ser. No. 08/650,364 filed on May 20, 1996 (now abandoned), which is a continuation of Ser. No. 08/143,313 filed on Oct. 25, 1993 (now abandoned), which application(s) is(are) incorporated herein by reference.

BACKGROUND OF THE INVENTION

1. Field of the Invention

This invention relates to a method for the preparation of microspheres, involving fluidized bed drying.

2. Description of Background and Related Art

The instant invention provides for a method for the preparation of microspheres wherein the microspheres are dried in a fluidized bed. The microspheres of the instant invention may encapsulate any kind of active agent, such as an antigen, adjuvant, peptide, polypeptide, hormone, antibiotic, and so on.

Polymer matrices for forming microspheres are described in the literature. U.S. Pat. Nos. 4,917,893 and 4,652,441 disclose a microcapsule produced by preparing a water-in-oil emulsion comprising an inner aqueous layer containing a water-soluble drug, a drug-retaining substance, and an oil layer containing a polymer substance; the inner or aqueous layer is thickened or solidified to a viscosity of not lower than about 5000 centipoises. The resulting emulsion is subjected to in-water drying. U.S. Pat. No. 4,954,298 discloses the production of microcapsules by preparing a water-in-oil emulsion composed of a water-soluble drug-containing solution as the inner aqueous phase and a polymer-containing solution as the oil phase, dispersing the emulsion in an aqueous phase and subjected the resulting water-in-oil-in-water emulsion to an in-water drying, wherein the viscosity of the water-in-oil emulsion used in preparing the water-in-oil-in-water emulsion is adjusted to about 150 to about 10,000 centipoises.

The microspheres of the art have typically been dried by v acuum drying or lyophilization. These methods are time consuming and often result in degradation, or "cracking", of the microspheres so dried.

Accordingly, it is an object of the invention to provide a method for drying microspheres.

It is another object to provide a drying procedure for microspheres that reduces the amount of time for drying and the amount of degradation of the microspheres.

These and other objects will be apparent to those skilled in the art.

SUMMARY OF THE INVENTION

Accordingly, the instant invention provides for a method for the preparation of microspheres wherein the microspheres a redried in a fluidized bed. The microspheres of the instant invention may encapsulate any kind of active agent, such as an antigen, adjuvant, peptide, polypeptide, hormone, antibiotic, and so on. A preferred polymer matrix for formation of the microspheres of the instant invention is poly(D-L-lactide-co-glycolide), although any polyester may be used. The microspheres of the instant invention are preferably formed by a water-in-oil-in-water emulsion p rocess. The drying step of the instant invention reduces the lengthy time required for more traditional methods of drying and reduces the amount of degradation of the microspheres.

One aspect of the invention is a method for encapsulating an active agent in microspheres, comprising (a) dissolving a polymer in an organic solvent to produce a solution;

(b) adding active agent to the solution of (a) to produce a polymer-active agent mixture comprising a first emulsion or suspension;

(c) adding the mixture of step (b) to an emulsification bath to produce a microspheres comprising a second emulsion;

(d) hardening the microspheres of step (c) to produce hardened microspheres comprising encapsulated active agent; and (e) drying the microspheres of step (d) in a fluidized bed.

Another aspect of the invention is a composition comprising microspheres encapsulating an active agent wherein the microspheres are dried in a fluidized bed.

Another aspect of the invention is a method for preparing polylactide microspheres, comprising drying the microspheres in a fluidized bed.

DETAILED DESCRIPTION OF THE PREFERRED EMBODIMENTS

A. DEFINITIONS

Figure 1:
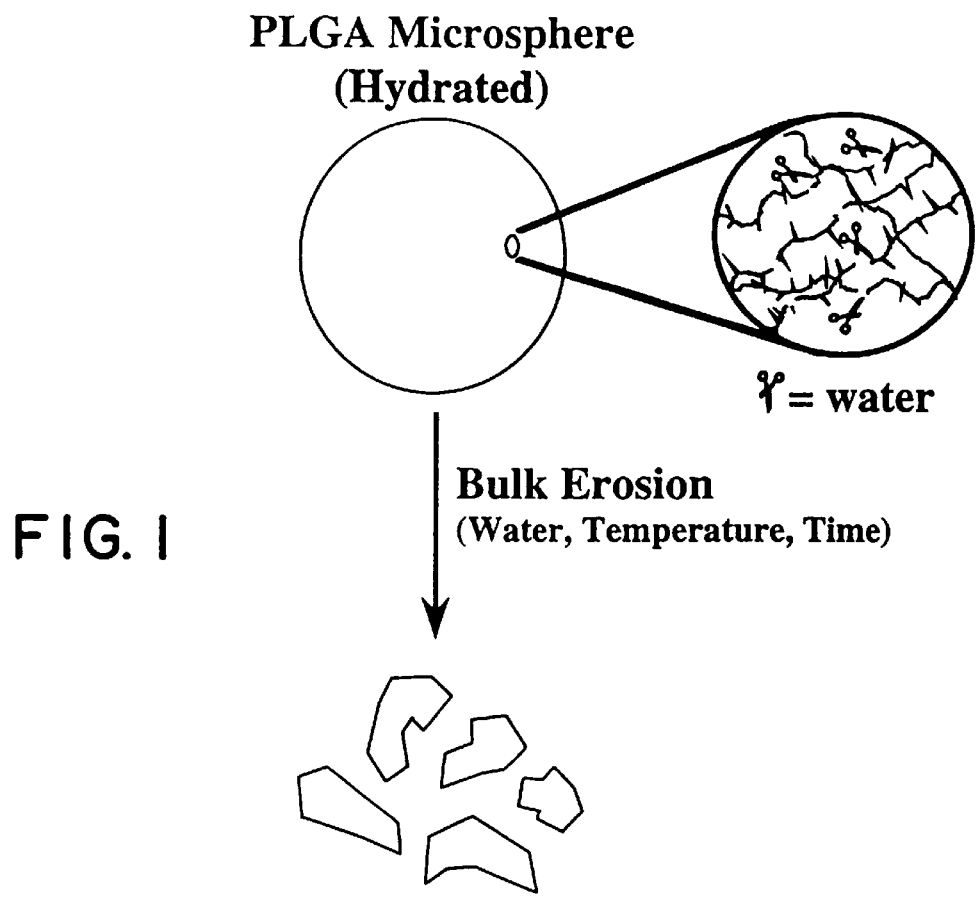
FIG. 1 is a diagram depicting the bulk erosion process for polylactide (PLGA) microspheres. PLGA microspheres are typically hydrated prior to administration. Water hydrolyzes the ester linkages in the PLGA backbone as shown in the inset diagram resulting in a bulk erosion of the polymer over time. The rate of hydrolysis depends upon the water content of the microspheres, the solvent environment (e.g., pH), and the temperature. The number of scissions in the polymer backbone required to cause fragmentation of the microspheres is dependent on the polymer molecular weight.
Figure 2:
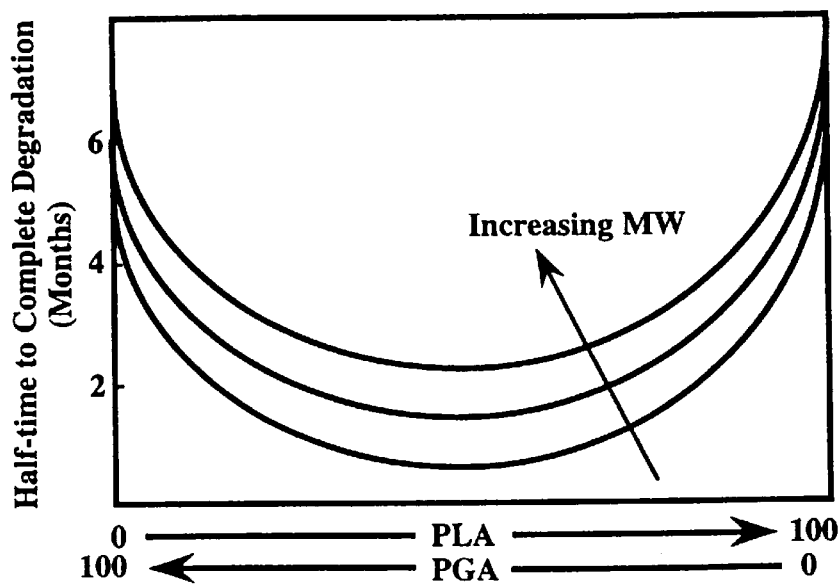
FIG. 2 is a diagram depicting in vivo degradation rate for PLGA polymers modified from Miller et al. (*J. Biomed. Mater. Res.* 11:711–719, 1977). The X-axis represents the relative ratio of either lactide or glycolide for each PLGA. The slowest degradation rates for a given polymer molecular weight occur for the polylactic acid (PLA) and polyglycolic acid (PGA) systems. The fastest degradation rate was achieved with PLGA containing an equal molar ratio of lactide and glycolide. The in vivo half-time to complete degradation was measured by histology studies in rats.

The terms "polylactide" and "PLGA" as used herein are us ed interchangeably and are intended to r efer to a polymer of lactic acid alone, a polymer of glycolic acid alone, a mixture of such polymers, a copolymer of glycolic acid and lactic acid, a mixture of such copolymers, or a mixture of such polymers and copolymers. A preferred polymer matrix for formation of the microspheres of the instant invention is poly(D-L-lactide-co-glycolide).

The term "active agent" as used herein denotes a compound of interest encapsulated in the microspheres of the invention, such as a therapeutic or biological active compound. Exemplary active agents include but are not limited to ligands, antigens, adjuvants, hormones, antibiotics, enzymes, and so on. "Active agent" is not limited to a single agent, but is intended to include a plurality of active agents, such as combinations of antigens, combinations of antigen (s) and adjuvants, and so on.

The term "encapsulation" as used herein denotes a method for formulating an active agent into a composition useful for controlled release of the active agent. Examples of encapsulating materials useful in the instant invention include any encapsulating material, preferably polyesters, and especially polymers referred to herein as "polylactides" or "PLGA."

"Fluidized bed" as used herein refers generally to a bed of granular particles through which a stream of gas is slowly flowing upward, such that with further increase in gas velocity, the pores and channels enlarge and the particles become more widely separated. Included in this definition are fluidized- or fixed-bed configurations, including but not limited to slurry and trickle-bed reactor systems. Gases used in the fluidized bed are preferably nitrogen, oxygen, and carbon dioxide, although any dry gas which facilitates removal of water and/or other solvents may be used. The methodology for designing a fluidized- or fixed-bed system is widely known in the art, as are examples of fluidized-bed systems useful in practicing the instant invention (see, for example, Perry & Chilton (Chemical Engineers' Handbook, R. H. Perry & C. H. Chilton, Eds., Fifth Edition, pp. 4–20–4–40, 5–52–5–55, 1973).

The term "excipient" as used herein denotes a nontherapeutic carrier added to a pharmaceutical composition that is pharmaceutically acceptable, i.e., non-toxic to recipients at the dosages and concentrations employed. Suitable excipients and their formulation are described in *Remington's Pharmaceutical Sciences*, 16th ed., 1980, Mack Publishing Co., Oslo, et al. ed.

The term "organic solvent" as used herein is intended to mean any solvent containing carbon compounds. Exemplary organic solvents include halogenated hydrocarbons, ethers, esters, alcohols and ketones, such as, for example, methylene chloride, ethyl acetate, a mixture of ethyl acetate and benzyl alcohol or acetone, dimethyl sulfoxide, tetrahydrofuran, dimethylformamide, and ethanol.

"Polypeptide" as used herein refers generally to peptides and proteins having at least about two amino acids.

The term "dry" or "drying" as used herein refers to removal of water sufficient to provide a final product with less than 20% (w/w) residual moisture.

The term "harden" as used herein in reference to microspheres refers to the extraction of excess organic solvent from the polymer phase.

B. GENERAL METHODS

Figure 3:
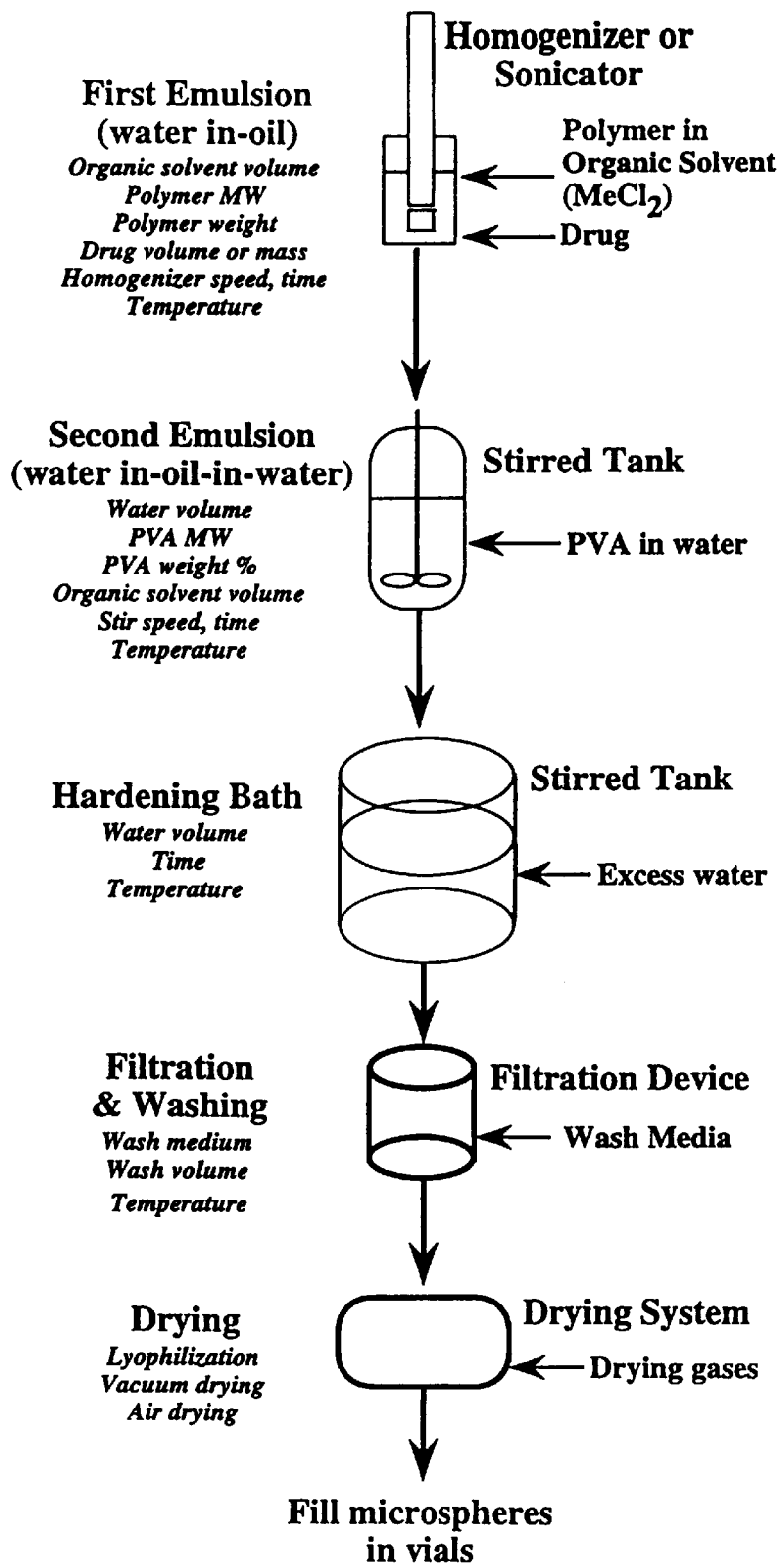
FIG. 3 is a diagram depicting the microsphere production process using a double emulsion method. PLGA polymers at different molecular weights were added to methylene chloride and allowed to dissolve. A solution of MN rgp120 or rhGH (human growth hormone) was then injected into the methylene chloride while homogenizing. The homogenized solution was added to a polyvinyl alcohol (PVA) solution. The PVA solution was saturated with methylene chloride (1.5% v/v) for some experiments. The PVA and polymer solutions were mixed in a one liter fermenter to form the final water-in-oil-in-water emulsion. The resulting microspheres were then transferred to the hardening bath which contained an excess of water to extract the remaining methylene chloride. The hardened microspheres were then washed and dried by lyophilization or low temperature (5° C.) nitrogen (fluidized bed) or vacuum drying to produce the final microspheres for in vivo and in vitro analysis. The items listed in italics are the variables for each process step.

In general, microencapsulation of an antigen or adjuvant is performed according to the protocol briefly outlined in FIG. 3. In summary, PLGA of the desired ratio of lactide to glycolide (about 100:0 to 0:100 weight percent, more preferably, about 65:35 to 35:65, most preferably about 50:50) and inherent viscosity (generally about 0.1 to 1.2 dL/g, preferably about 0.2 to 0.8 dL/g) is first dissolved in an organic solvent such as methylene chloride, or ethyl acetate with or without benzyl alcohol or acetone to the desired concentration (generally about 0.05 to 1.0 g/mL, preferably about 0.3 to 0.6 g/mL). A concentrated antigen or adjuvant solution (for example, typically at least 0.1 mg/mL for polypeptides, preferably greater than about 100 mg/mL, depending, for example, on the type of polypeptide and the desired core loading) is then suitably injected (such as with a 25 gauge needle) into the polymer solution while homogenizing at about 15,000 to 25,000 rpm. Dry antigen or adjuvant can be used in place of aqueous antigen or adjuvant. After homogenization (generally about 0.5 to 5 minutes, more preferably for 1 minute), the emulsion is added to the reaction kettle (emulsification bath) or static mixer (not shown) to form a second emulsion. The emulsification bath is typically a polyvinyl alcohol solution, optionally including ethyl acetate. The reaction kettle is mixed at high speed (generally about 1700 to 2500 rpm) to generate small microspheres (about 20 to 100 µm median diameter). The second emulsion is transferred to a hardening bath after a sufficient period of time, generally about 0.5 to 10 minutes, preferably about 1 minute, and allowed to gently mix for a suitable time, generally about 1 to 24 hours, preferably about 1 hour. When hardening is complete, the microspheres are prefiltered (such as with a 150 µm mesh), concentrated and diafiltered. Diafiltering is suitably accomplished in an Amicon stirred cell (2500 mL), preferably with about a 16 or 20 µm filter. The microspheres are washed, typically with about 1 to 100 L, preferably about 15 L of prefiltered water and typically with about 1 to 100 L, more preferably 15 L of 0.1% Tween® 20. The final microspheres are removed from the filter and resuspended in water and filled in vials, preferably at about 500 µL/ vial in 3 cc vials. The microspheres can then be dried. Drying includes such methods as lyophilization, vacuum drying, and fluidized bed drying.

Three other exemplary methods can be employed to produce microspheres. The first method utilizes a solvent evaporation technique. A solid or liquid active agent is added to an organic solvent containing the polymer. The active agent is then emulsified in the organic solvent. This emulsion is then sprayed onto a surface to create microspheres and the residual organic solvent is removed under vacuum. The second method involves a phase-separation process, often referred to as coacervation. A first emulsion of aqueous or solid active agent dispersed in organic solvent containing the polymer is added to a solution of non-solvent, usually silicone oil. By employing solvents that do not dissolve the polymer (non-solvents) but extract the organic solvent used to dissolve the polymer (e.g. methylene chloride or ethyl acetate), the polymer then precipitates out of solution and will form microspheres if the process occurs while mixing. The third method utilizes a coating technique. A first emulsion comprising the active agent dispersed in a organic solvent with the polymer is processed through an air-suspension coater apparatus resulting in the final microspheres.

The degradation rate for the microspheres of the invention is determined in part by the ratio of lactide to glycolide in the polymer and the molecular weight of the polymer. Polymers of different molecular weights (or inherent viscosities) can be mixed to yield a desired degradation profile.

The microspheres of the instant invention can be prepared in any desired size, ranging from about 0.1 to upwards of about 100 μm in diameter, by varying process parameters such as stir speed, volume of solvent used in the second emulsion step, temperature, concentration of polymer(s), and inherent viscosity of the polymer(s).

The formulations of the instant invention can contain a preservative, a buffer or buffers, multiple excipients, such as polyethylene glycol (PEG) in addition to trehalose or mannitol, or a nonionic surfactant such as Tween® surfactant. Non-ionic surfactants include polysorbates, such as polysorbate 20 or 80, and the poloxamers, such as poloxamer 184 or 188, Pluronic® polyols, and other ethylene oxide/propylene oxide block copolymers, etc. Amounts effective to provide a stable, aqueous formulation will be used, usually in the range of from about 0.1% (w/v) to about 30% (w/v).

The pH of the formulations of this invention is generally about 5 to 8, preferably about 6.5 to 7.5. Suitable buffers to achieve this pH include, for example, phosphate, Tris, citrate, succinate, acetate, or histidine buffers, depending on the pH desired. Preferably, the buffer is in the range of about 2 mM to about 100 mM.

Examples of suitable preservatives for the formulation include phenol, benzyl alcohol, meta-cresol, methyl paraben, propyl paraben, benzalconium chloride, and benzethonium chloride. Preferred preservatives include about 0.2 to 0.4% (w/v) phenol and about 0.7 to 1% (w/v) benzyl alcohol, although the type of preservative and the concentration range are not critical.

In general, the formulations of the subject invention can contain other components in amounts not detracting from the preparation of stable forms and in amounts suitable for effective, safe pharmaceutical administration. For example, other pharmaceutically acceptable excipients well known to those skilled in the art can form a part of the subject compositions. These include, for example, salts, various bulking agents, additional buffering agents, chelating agents, antioxidants, cosolvents and the like; specific examples of these include tris-(hydroxymethyl)aminomethane salts ("Tris buffer"), and disodium edetate.

The microspheres are placed into pharmaceutically acceptable, sterile, isotonic formulations together with any required cofactors, and optionally are administered by standard means well known in the field. Microsphere formulations are typically stored as a dry powder.

Further details of the invention can be found in the following examples, which further define the scope of the invention. All references cited herein are expressly incorporated by reference in their entirety.

EXAMPLES
1. MATERIALS AND METHODS
   a. Materials
   Poly(D-L-lactide-co-glycolide) (PLGA) was purchased from both Boehringer Ingelheim (BI) and Medisorb Technologies International L.P. (MTI). PLGA at 12 kD and 100 kD were obtained from BI and PLGA at 18 kD and 100 kD were obtained from MTI. The polymer compositions were either 50:50, 65:35, or 75:25 lactide:glycolide. The 10% polyvinyl alcohol solution (PVA Airvol 205, Air Products) was prepared by dissolving solid PVA in warm water (approximately 80° C.). The final PVA solution was filtered with 0.22 μm Millipak filters from Millipore. Methylene chloride (technical grade) was purchased from Baxter S/P.

MN rgp120 (Lot# Y16531/G90557) was supplied in bulk at 2.3 mg/mL protein in 20 mM Tris, 0.120 M NaCl, pH 7.4 from Genentech, Inc. It was concentrated with a Amicon stirred cell concentrator using a YM 30,000 MW cutoff membrane at 4° C. to a final concentration of 154 mg/mL and stored at 2 to 8° C.

Lyophilized QS21 (approximately 80% pure, Lot# D1949) was supplied from Cambridge Biotech (Cambridge, Mass.). QS21 was prepared at 200 mg/mL by dissolving the lyophilized QS21 powder in 50% ethanol/water. QS21 was also dissolved in 50% ethanol with 20% Tween® 20 in an attempt to increase the encapsulation efficiency and release rate. The QS21 solutions were prepared and used on the same day as the encapsulation.

rhGH was supplied in bulk from Genentech, Inc., at 5–10 mg/mL protein in 10 mM ammonium bicarbonate, pH 7. The protein was filtered with a 0.22 μm filter, filled at 20 mL in 100 cc vials and lyophilized to produce a dry powder. The lyophilized protein was reconstituted to 10 mg/mL protein with 5 mM potassium phosphate buffer, 2.5 mg/mL trehalose, pH 8. The protein was then filtered with a 0.22 μm filter, filled at 20 mL in 100 cc vials, and lyophilized again to produce a dry powder. This final powder was reconstituted to 400 mg/mL rhGH with 5 mM potassium phosphate buffer at pH 8. This rhGH solution contained 100 mg/mL trehalose and about 100 mM potassium phosphate, pH 8.

b. Microencapsulation
The production of rgp120 microspheres was performed by a double emulsion water-in-oil-in-water (WOW) as discussed above in general terms. More specifically, the PLGA concentrations in methylene chloride were 0.3 or 0.6 g/mL, and the first emulsion was homogenized at 15,000 rpm and 0 to 1° C. in a water bath. After 1 minute of homogenization, the first emulsion (10 mL) was added to 900mL of 10% PVA solution containing 1.5% methylene chloride and emulsified at high speed (800 to 2500 rpm), for 1 minute in the reaction kettle (2 to 8° C.). To improve the encapsulation efficiency, the second emulsion was also performed with 10% PVA that did not contain methylene chloride and the temperature of the second emulsion was maintained at 0 to 3° C. To achieve the reduced temperature, the ethylene glycol in the cooling jacket of the reaction kettle was kept at −15° C. The second emulsion was then transferred to the hardening bath containing 12 liters of prefiltered water (MilliQ water system, Millipore Corp.) at 2 to 8° C. The microspheres were allowed to harden for 1 hour. The hardened microspheres were concentrated to about 1.5 L and diafiltered against 15 L of prefiltered water followed by 15 L of 0.1% Tween® 20. The Amicon stirred cell (2.5-L) was operated with different filter systems depending upon the desired particle size. After washing, the microspheres were concentrated to dryness. The concentrated microspheres were removed from the filter by using a cell scraper and resuspended in prefiltered water to approximately 0.3 gm/mL.

QS21 was dissolved in 50% ethanol with or without Tween® 20 as described above. As with the rgp120 solutions, the QS21 solution was injected into the polymer phase. For the microsphere preparations containing both rgp120 and QS21, the rgp120 solution was injected into the polymer phase after the QS21 solution to reduce the potential interaction between rgp120 and the ethanol in the QS21 solution. The microencapsulation of QS21 was performed with conditions similar to those described above for rgp120.

The microencapsulation of rhGH in PLGA was performed by using a double emulsion water-in-oil-in water (W/O/W) system as illustrated in FIG. 3. The polymer was added to the organic solvent (methylene chloride or ethyl acetate) and then the solution was cooled to 1° C. The solution was homogenized at 7000 rpm while maintaining the solution at 1° C. The protein solution (water phase) was then injected in 30–60 seconds into the polymer phase near the tip of the homogenizer operating at 7000 rpm. The homogenization continued for an additional 1 min and the primary emulsion was generated. The 6% PVA solution (with or without methylene chloride) was cooled to 0 to 3° C. and stirred at a constant speed (1800–2500 rpm). The primary emulsion was then introduced into the PVA solution (via metal injector, nitrogen pressurization or peristatic pumping) near the lower impeller and the secondary emulsion was created. The emulsification continued for an additional 1 min. The double emulsion was then transferred to the hardening bath which was stirred at a constant speed and maintained at 2 to 8° C. The microspheres were allowed to harden for 1 hr at 5° C. with constant stirring. The content of the hardening bath was siphoned through a 150 µm mesh and into the holding tank. The microspheres were then concentrated and washed in a 2.5 liter Amicon stir cell (fitted with a 25 µm mesh). Several cycles of low and high volumes of the wash solution in the stir cell were performed to provide efficient removal of microspheres that were smaller than 25 µm. Washed microspheres were harvested by washing the 25-µm filter with about 100 mL of 0.1% Tween 20, collected in a 250 mL beaker and allowed to settle at 5° C. for about 1hr. The supernatant, which contained small microspheres that did not settle, was removed by aspiration and the remaining microspheres were prepared for drying. In some experiments, the hardening bath and washing steps were replaced with a vortex flow filtration system. The double emulsion was poured into a hardening bath containing 6 liter of MilliQ water and sent to the vortex flow filtration system. The content was pumped through the feed inlet and passed over a rotating 25 µm cartridge membrane. Microspheres smaller than 25 µm passed through the membrane (permeate), while the rest of the microspheres were recirculated back into the hardening bath for further hardening and filtration. A constant supply of fresh water (or 0.1% Tween 20) was delivered to the hardening bath and the liquid level was maintained. At the end of this process, the microspheres were collected, filtered through a 150-µm mesh, and allowed to settle, and the supernatant was removed. The final microspheres were then dried.

c. Drying Methods

Figure 4:
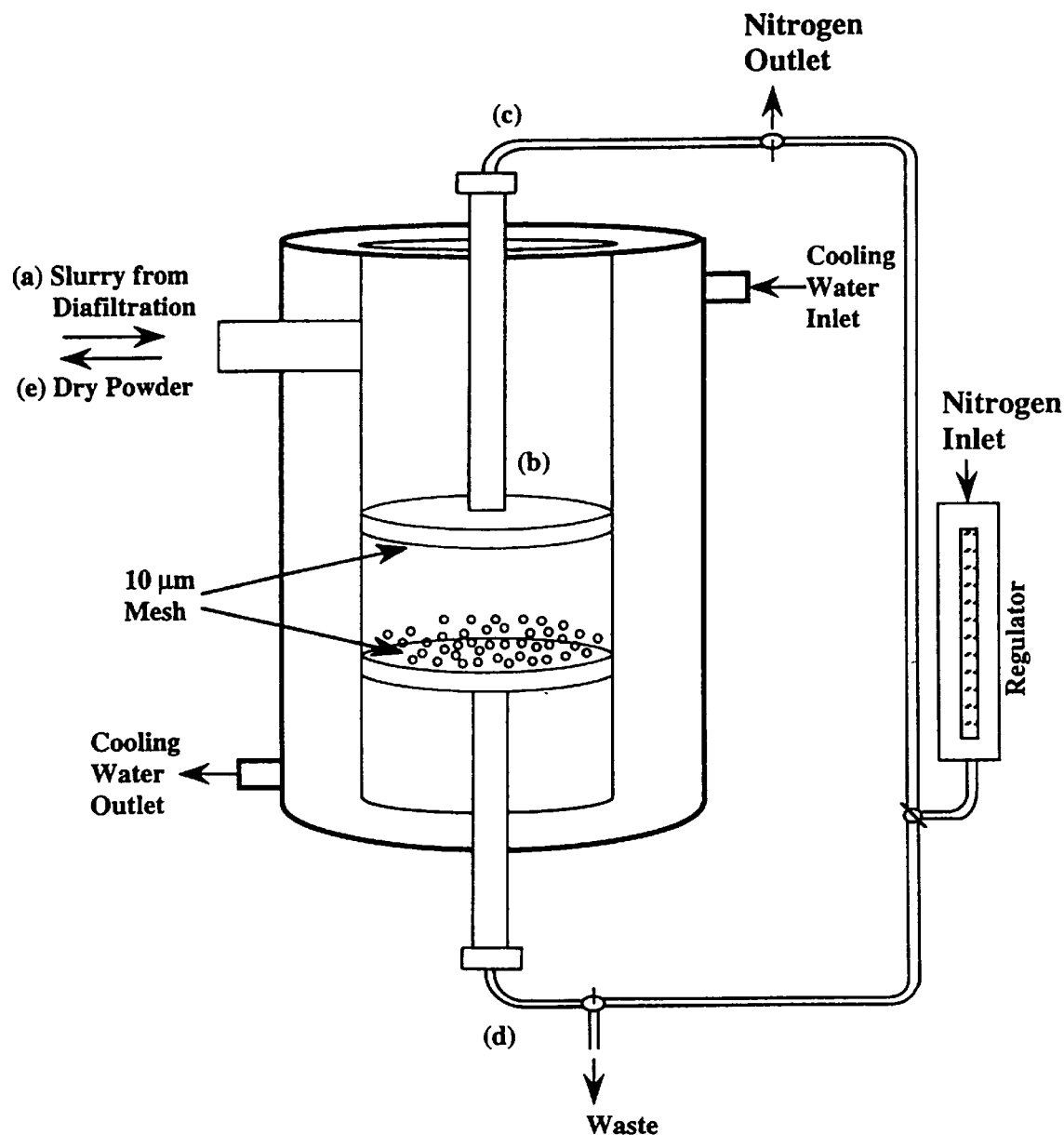
FIG. 4 is a diagram depicting an air lift (fluidized bed) drying system for nitrogen drying of PLGA microspheres. (a) Slurry from a diafiltration unit is pumped into the chamber with the upper piston (b) above the inlet. The upper piston is then moved down and the excess liquid is pressurized out by applying nitrogen through the upper inlet (c). The airflow is then redirected to suspend the microspheres by purging with nitrogen through the lower inlet (d) and releasing the nitrogen through the upper inlet (c). After complete drying (1 to 2 days), the dry powder is removed by placing a collection vessel (side arm flask, not shown) on the outlet, moving the upper piston (b) above the outlet, and applying nitrogen pressure at the lower inlet (d) while pulling a vacuum on the collection vessel. Alternatively, the drier can be designed with both pistons welded in place and the upper piston located above the inlet for the slurry. After pumping in the slurry, the slurry outlet side arm is then sealed by a valve during drying.

Three different drying methods were used to dry the microspheres: lyophilization, vacuum drying, and fluidized bed drying by using the system shown in FIG. 4 or a 5 mL Amicon stirred cell. Lyophilization and vacuum drying were performed by placing an aqueous suspension of the microspheres in 3-mL vials with vented stoppers. For lyophilization, the suspensions were frozen at −55° C. for 4.75 hours followed by warming to −20° C. While at −20° C., a vacuum of 250 mTorr was applied for 12 hours. After completion of the bulk water removal stage (primary drying), the samples were warmed to 20° C. and held under a vacuum of 250 mTorr for 6 hours. Vacuum drying was conducted by placing the vials in a sealed desiccator at 2–8° C. and applying a vacuum for 1 week to obtain residual moistures of <20%. For fluidized bed drying, a suspension of the final microspheres was added to the airlift drier (FIG. 4) or a stirred cell and the residual liquid was removed by applying a slight (approximately 2 psi) nitrogen pressure to the column (nitrogen flow downward). After the residual liquid was removed, the nitrogen flow was directed upward through the airlift drier or Amicon stirred cell to suspend the microspheres. The nitrogen line was connected to a prefilter (0.22 µm) for the stirred cell and a desiccating column with prefilters for the airlift drier. A water bath was connected to the jacket of the airlift drier to maintain the system at 5° C. The Amicon stirred cell drying was performed in a 2 to 8° C. cold room.

d. Microsphere Loadina

The protein content of the MN rgp120-PLGA and rhGH-PLGA microspheres was determined as follows. Dried microspheres were added (10 to 20 mg) to 1 mL of 1 N NaOH and allowed to dissolve by shaking at room temperature for 2 to 16 hours. Standards of MN rgp120 or rhGH were prepared by adding 5 N NaOH to the stock solutions of each protein (1.5 mg/mL MN rgp120; 5 mg/mL rhGH) to yield a 1 N NaOH solution. In 1 N NaOH, tyrosine is deprotonated resulting in a significant shift in the absorbance maximum and, thus, protein dissolved in 1 N NaOH will have a different absorbance spectrum than native protein in buffer at neutral pH. Standard solutions containing different concentrations of MN rgp120 or rhGH in 1 N NaOH were used to determine the shifted absorbance maxima of the protein and,the extinction coefficient at this wavelength. The extinction coefficient for MN rgp120 in 1 N NaOH was 1.39 cm−1(mg/mL)−1 at 284 nm. The extinction coefficient for rhGH in 1 N NaOH was 1.114 cm−1(mg/mL)−1 at 294 nm.

The amount of protein released from the microspheres was determined by the Pierce Chemical Co. BCA Protein Assay. Both lyophilized and "wet" microspheres were analyzed. "Wet" microspheres were defined as microspheres that were removed from the diafiltration cell and suspended in release medium without additional processing. The amount of protein released was then used to calculate the percent of MN rgp120 or rhGH released (percent of total) from the microspheres based on the mass of microspheres in the release device, the protein loading of the microspheres, and the volume of the release medium (20 mg of microspheres in 300 µl of 10 mM Hepes, 100 mM NaCl, 0.02% (w/w) Tween® 20, 0.02% NaN3, pH 7.4).

The amount of QS21 encapsulated in the PLGA microspheres was determined by dissolving the microspheres in 1 N NaOH at room temperature overnight. The completely dissolved solutions were neutralized with 6 N HCl. The samples were then injected onto a SEC column, TSK G3000SW XL (0.78×30 cm), equilibrated in 0.4 M KPO$_4$, pH 7.0. The column running conditions were the same as those used for the SEC analysis of rgp120. Since QS21 degrades in 1 N NaOH, the chromatographs from SEC analysis contained several peaks. To quantify the total amount of QS21, the peak areas corresponding to QS21 and its degradation products were used in the determination of the core loading. As standards, known amounts of QS21 were added to placebo microspheres and then treated with 1 N NaOH. SEC analysis was performed on the standards and the peak areas from the standards were used to calculate the amount of QS21 in each sample.

QS21 released from microspheres was quantitated by a 5 µm YMC C4 (0.46×25 cm) RP-HPLC with 1 mL/min flow rate and detection at 214 nm. A linear gradient was run in 15 minutes from 25 to 75% of solution B (Solution A: 0.1% TFA in water; Solution B: 0.1% TFA in 90% acetonitrile).

QS21 controls were also run. In RP-HPLC analysis, the rgp120 peak elutes before the QS21 peak and, therefore, this method provides simultaneous quantitation of QS21 and rgp120 released from the microspheres.

2. RESULTS a. Effect of Drying on Initial Burst and Quality of the Microspheres

To investigate the correlations among the initial burst, polymer, and drying technique, drying experiments were performed on several microsphere preparations. The drying techniques used in these studies were lyophilization, vacuum drying, and fluidized-bed drying. The amount of initial protein released (1 hour incubation) from microspheres dried with each of these techniques was compared to the initial burst (1 hr) from microspheres that were analyzed immediately after production (wet).

One method used to reduce the microsphere drying time was lyophilization, which usually requires only one to two days. Lyophilization or vacuum drying of the low molecular weight PLGA formulations resulted in a 1.5 to 8-fold increase in the initial burst. Aqueous protein droplets encapsulated at or near the surface of the microspheres probably cause the initial burst from these microspheres. If the viscosity of the first emulsion is increased, the aqueous droplets formed during homogenization are less likely to coalesce. Thus, small droplets at or near the surface will release less total protein for microspheres containing the same total aqueous volume. To increase the viscosity of the first emulsion, the PLGA concentration in the methylene chloride can be raised. By increasing the PLGA (12 kD) concentration from 0.3 to 0.6 g/mL, the initial burst from lyophilized or vacuum dried microspheres was reduced from greater than 50% to 30 to 50%. Initial microspheres produced at 0.3 g/mL 12 kD (50:50 lactide:glycolide) PLGA in the first emulsion were also cracked and broken after lyophilization. During lyophilization, the microspheres are frozen and the excess water is removed by sublimation. The formation of ice crystals within the microspheres can contribute to cracking or complete fracture of the microspheres. The stability of the aqueous droplets can be increased by increasing the viscosity of the first emulsion through reductions in temperature and by removing the excess methylene chloride from the second emulsion, causing a more rapid formation of microspheres. When the process conditions were modified to include both these changes, the microspheres were not broken or cracked after lyophilization or vacuum drying, but did have a large initial burst (greater than 65%). The large initial burst is likely the result of the instability of the first emulsion encapsulated within the microspheres. More aqueous droplets can accumulate at the surface if the polymer is warmed above 2 to 8° C. and, thus, provide the large initial burst that was observed in the intact microspheres.

In contrast, lyophilization did not cause cracking or breakage of microspheres produced with either an equal mass ratio blend of high and low molecular weight PLGA or high molecular weight PLGA alone when produced at low temperature without excess methylene chloride in the second emulsion. These microsphere preparations also did not have a large initial burst (less than 30%, Table 1). In addition, microspheres produced with the high molecular weight PLGA had a much lower initial burst after lyophilization or vacuum drying (Table 1). Both the equal mass ratio blend of high and low molecular weight polymer and the high molecular weight polymer preparations did not reveal a correlation between protein loading and initial burst for loadings ranging from 1.8 to 3.9% w/w. However, at very low protein loading (0.5% w/w), microspheres produced with the same conditions had a greatly reduced initial burst. Because the initial burst is controlled by the diffusion of protein out of the microspheres, the rate of release (initial burst) will be dependent upon the concentration difference between the bulk solution and the hydrated, accessible protein (surface protein). The amount of protein at the surface will also be reduced since the protein concentration in the aqueous droplets is reduced.

TABLE 1

Effect of Drying Method on Initial Burst[a]

| Polymer (lactide:glycolide) | Protein Loading[b] (% w/w) | Initial Burst (1 hr) | | |
|---|---|---|---|---|
| | | wet[c] | lyophilized[d] | fluidized bed[e] |
| 12/100 kD (50:50) BI[f] | 3.1 | 16 | 19 | 12 |
| | 3.5 | 5 | 22 | 10 |
| | 1.8 | 15 | 15 | 10 |
| | 1.8 | 19 | 23 | 22 |
| | 0.5[g] | 2 | 0.4 | 1 |
| 18/100 kD (50:50) MTI[f] | 3.8 | 12 | 23 | 8 |
| | 3.9 | 9 | 32 | 17 |
| | 1.8 | 5 | 15 | 7 |
| | 1.8 | 7 | 13 | 4 |
| 100 kD (50:50) MTI | 1.8 | 10 | 10 | 2.4 |

[a]Microspheres were prepared as described in Materials and Methods (0.3 g PLGA/mL methylene chloride, 0.1 mL gp120 protein solution/mL methylene chloride, reduced temperature, no excess methylene chloride in second emulsion).
[b]All preparations had greater than 95% encapsulation efficiency.
[c]Microspheres were analyzed immediately after production without drying.
[d]Lyophilization was performed with the following cycle: 4.75 hr at −55° C., 12 hr at −20° C. with 250 mTorr, and 6 hr at 20° C. with 250 mTorr.
[e]Fluidized bed drying was performed by passing nitrogen through the microspheres on a 20 μm mesh in either a fluidized bed system (see FIG. 4) or in an Amicon stirred cell where the nitrogen flow is directed upward.
[f]A 50:50 mass ratio of the low and high molecular weight PLGA was used to produce these microspheres.
[g]Values for the initial burst from these microspheres were very low and difficult to measure. Thus, these values are only accurate to +1% (e.g., 2 ± 1% initial burst).

b. Comparison of Drying Methods

In separate experiments, microspheres were prepared under different process conditions and analyzed for the effect of drying conditions on the initial burst. The results in Table 2 demonstrate a consistent reduction in the initial burst when lyophilized or vacuum dried microspheres are compared with microspheres dried with nitrogen in a fluidized bed. Table 3 describes the process conditions used in Table 2. In these experiments, the process was operated at low temperature (1° C. for first emulsion; 3° C. for second emulsion) and the protein formulation was 400 mg/mL rhGH, 100 mg/mL trehalose, 100 mM potassium phosphate, pH 8.

TABLE 2

Effect of Drying Method on Initial Burst from rhGH-PLGA Microspheres Prepared by the Water-in-Oil-in-Water Double Emulsion Method

| Core Loading | Initial Burst from Drying Method[a] (% of Total) | | | | Process |
|---|---|---|---|---|---|
| (% w/w) | Wet[b] | Lyo.[c] | Vacuum[d] | Fluidized Bed[e] | Conditions[f] |
| 7.0 | 31.4 | 64.7 | ND[g] | 41.7 | A |
| 7.4 | 57.8 | 73.9 | ND | 54.3 | B |
| 9.0 | 27.3 | ND | 51.1 | 31.5 | C |
| 9.1 | 53.5 | 87.3 | ND | 65.2 | D |
| 9.2 | 17.8 | 36.9 | ND | 16.5 | F |
| 9.5 | 17.2 | ND | 23.3 | 8.4 | E |

TABLE 2-continued

Effect of Drying Method on Initial Burst from rhGH-PLGA Microspheres Prepared by the Water-in-Oil-in-Water Double Emulsion Method

| Core Loading | Initial Burst from Drying Method[a] (% of Total) | | | | Process |
|---|---|---|---|---|---|
| (% w/w) | Wet[b] | Lyo.[c] | Vacuum[d] | Fluidized Bed[e] | Conditions[f] |
| 10.2 | 15.5 | 35.7 | ND | 10.6 | E |
| 10.3 | 29.2 | 41.9 | ND | 24.3 | F |

[a]Microspheres were incubated in release media for 1 hour and the amount of protein released was measured (% release = 100% * (mass protein release/total mass in microspheres)).
[b]Microspheres were analyzed immediateiy after production without drying.
[c]Lyophilization was performed with the following cycle: 4.75 hr at −55° C., 12 hr at −20° C. with 250 mTorr, and 6 hr at 20° C. with 250 mTorr.
[d]Vacuum drying was done by placing partially stoppered vials in a desiccator and pulling a vacuum at 2–8° C.
[e]Fluidized bed drying was performed by passing nitrogen through the microspheres on a 20 μm mesh in either a fluidized bed system (see FIG. 4) or in an Amicon stirred cell where the nitrogen flow is directed upward.
[f]Microspheres were prepared at several different process conditions and the letters (A–F) refer to the conditions listed in Table 3.
[g]ND indicates "not determined."

TABLE 3

Process Conditions for rhGH-PLGA Microspheres from Table 2

| Process Condition | $V_a/V_o$ (mL/mL) | [PLGA] (g/mL) | Second Emulsion | | | Polymer (dL/g; lactide:glycolide; Vendor) |
|---|---|---|---|---|---|---|
| | | | PVA %[a] | Device[b] | Solvent[c] | |
| A | 0.25 | 0.58 | 6.0 | SM | EtAc | 0.21; 65:35; MTI |
| B | 0.10 | 0.30 | 9.0 | SM | EtAc[d] | 0.21; 48:52; BI |
| C | 0.26 | 0.58 | 6.0 | F | MeCl$_2$ | 80:20 mass ratio of 0.21; 48:52; BI D,L-lactide |
| D | 0.10 | 0.30 | 9.0 | SM | EtAc[d] | 90:10 mass ratio of 0.21; 48:52; BI 0.53; 51:49; MTI |
| E | 0.26 | 0.58 | 6.0 | F | MeCl$_2$ | 0.21; 48:52; BI |
| F | 0.27 | 0.40 | 6.0 | SM | MeCl$_2$ | 0.21; 48:52; BI |

[a]Polyvinyl alcohol was dissolved in prefiltered water (MilliQ water, Millipore). When ethyl acetate was used as the solvent, the PVA solution contained 10% ethyl acetate. Methylene chloride was not added to the PVA solution for these preparations.
[b]The mixing device used to produce the second emulsion (water-in-oil-in-water) was either a static mixer (SM) or a fermenter (F).
[c]The polymer was dissolved in either ethyl acetate (EtAc) or methylene chloride (MeCl$_2$).
[d]5% acetone was added to the ethyl acetate/PLGA solution to facilitate dissolution of the PLGA.

Table 4 provides similar data for solid human growth hormone. The starting lyophilized protein formulation (trehalose, rhGH, and phosphate) was produced by a rapid freezing method which resulted in the formation of small solid particles. Microspheres were prepared by dissolving 4 g of PLGA (0.21 dL/g) in 10 mL of ethyl acetate and adding either 500 mg (e) or 750 mg (f) of lyophilized rhGH. The mixture was then homogenized at 7000 rpm for 90 seconds at 1° C. The PLGA phase was then pumped to the inlet of a static mixer at 15 mL/min while a 9% PVA solution containing 10% ethyl acetate was pumped to the same inlet at 2 L/min. The outlet of the static mixer was attached to a stirred tank (hardening bath) containing 12 L of prefiltered water. After one hour in the hardening bath, the microspheres were filtered with a 150-μm mesh and then diafiltered with a 20-μm mesh and 60 L of 0.1% Tween at 2–8° C. The final microspheres were then dried as indicated in the Table.

TABLE 4

Effect of Drying Method on Initial Burst from rhGH-PLGA Microspheres Prepared by the Solid-in-Oil-in-Water Emulsion Method

| Core Loading | Initial Burst from Drying Method[a] (% of Total) | | |
|---|---|---|---|
| (% w/w) | Wet[b] | Lyo.[c] | Fluidized Bed[d] |
| 1.8[e] | 15.7 | 56.7 | 20.2 |
| 2.3[f] | 17.9 | 62.5 | 15.8 |

[a]Microspheres were incubated in release media for 1 hour and the amount of protein released was measured (% release = 100% * (mass protein release/total mass in microspheres)).
[b]Microspheres were analyzed immediately after production without drying.
[c]Lyophilization was performed with the following cycle: 4.75 hr at −55° C., 12 hr at 20° C. with 250 mTorr, and 6 hr at 20° C. with 250 mTorr.
[d]Fluidized bed drying was performed by passing nitrogen through the microspheres on a 20 μm mesh in either a fluidized bed system (see FIG. 4) or in an Amicon stirred cell where the nitrogen flow is directed upward.
[e]500 mg hGH was added in the first emulsion.
[f]750 mg hGH was added in the first emulsion.

Table 5 provides similar data for MN rgp120 encapsulated by the double emulsion method. Microspheres were prepared by dissolving 3 g of PLGA in 10 mL of methylene chloride. 1 mL of MN rgp120 was injected into the PLGA solution while homogenizing at 15,000 rpm. After injection, the emulsion was homogenized for 1 min. The PLGA consisted of a 50:50 mass ratio of 0.21 dL/g (48:52 lactide/glycolide) and 0.76 dL/g (48:52 lactide/glycolide) from BI (e) or 0.24 dL/g (50:50 lactide/glycolide) and 0.75 dL/g (51:49 lactide/glycolide) from MTI (f). The first emulsion was performed at 1° C. The first emulsion was added to a well mixed fermenter containing 900 mL of a 9% PVA solution at 3° C. After mixing for 1 min, the second emulsion was added to 12 L of prefiltered water at 2–8° C. and allowed to harden for 1 hr. The microspheres were then filtered with a 150-μm mesh and then diafiltered with a 20-μm mesh and 30 L of 0.1% Tween at 2–8° C. The final microspheres were then dried as indicated in the Table.

TABLE 5

Effect of Drying Method on Initial Burst from MN rgp-12-PLGA Microspheres Prepared by the Water-in-Oil-in-Water Double Emulsion Method

| Core Loading | Initial Burst from Drying Method[a] (% of Total) | | |
|---|---|---|---|
| (% w/w) | Wet[b] | Lyo.[c] | Fluidized Bed[d] |
| 3.1[e] | 2.9 | 56.7 | 31.0 |
| 3.1[e] | 12.6 | 20.9 | 13.3 |
| 3.5[e] | 5.1 | 21.8 | 10.4 |
| 3.8[f] | 11.0 | 22.5 | 7.6 |
| 3.9[f] | 6.5 | 22.9 | 17.3 |

[a]Microspheres were incubated in release media for 1 hour and the amount of protein released was measured (% release = 100% * (mass protein release/total mass in microspheres)).
[b]Microspheres were analyzed immediately after production without drying.
[c]Lyophilization was performed with the following cycle: 4.75 hr at 55° C., 12 hr at 20° C. with 250 mTorr, and 6 hr at 20° C. with 250 mTorr.
[d]Fluidized bed drying was performed by passing nitrogen through the microspheres on a 20 μm mesh in either a fluidized bed system (see FIG. 4) or in an Amicon stirred cell where the nitrogen flow is directed upward.

Table 6 provides similar data for microspheres encapsulating the adjuvant QS21 and MN gp120. Microspheres were prepared by dissolving 3 g of PLGA in 10 mL of methylene chloride. 0.5 mL of MN rgp120 (Batch 1: 76 mg; Batch 2: 56 mg) and 0.5 mL of QS21 (Batch 1: 94 mg; Batch 2: 105 mg) was injected into the PLGA solution while homogenizing at 15,000 rpm. After injection, the emulsion was homogenized for 1 min. The PLGA consisted of a 50:50 mass ratio of 12 kD (75:25 lactide:glycolide) and 100 kD (75:25 lactide:glycolide) from BI (Batch 1) or 12 kD (0.21 dL/g; 48:52 lactide/glycolide) and 100 kD (0.76 dL/g; 48:52 lactide:glycolide) from BI (Batch 2). The first emulsion was performed at 1° C. The first emulsion was added to a well mixed fermenter containing 900 mL of a 9% PVA solution at 3° C. After mixing for 1 min, the second emulsion was added to 12 L of prefiltered water at 2–8° C. and allowed to harden for 1 hr. The microspheres were then filtered with a 150-μm mesh and then diafiltered with a 20-μm mesh and 30 L of 0.1% Tween at 2–80° C. The final microspheres were then dried as indicated in the Table.

TABLE 6

Effect of Drying Method on Initial Burst from QS21/MN rgp120-PLGA Microspheres Prepared by the Water-in-Oil-in-Water Double Emulsion Method

| Core Loading | Initial Burst from Drying Method[a] (% of Total) | | | |
|---|---|---|---|---|
| (% w/w) | Wet[b] | Lyo.[c] | Vacuum[d] | Fluidized Bed[e] |
| Batch 1 | | | | |
| gp120: 2.5 | 2.4 | 29.1 | 28.8 | ND[f] |
| QS21: 1.9 | ND | 28.6 | 41.0 | ND |
| Batch 2 | | | | |
| gp120[g]: 1.8 | 16.6 | 20.2 | ND | 14.9 |
| QS21: 3.5 | ND | 16.4 | ND | 10.1 |

[a]Microspheres were incubated in release media for 1 hour and the amount of protein or QS21 released was measured (% release = 100% * (mass released/total mass in microspheres)).
[b]Microspheres were analyzed immediately after production without drying.
[c]Lyophilization was performed with the following cycle: 4.75 hr at −55° C., 12 hr at 20° C. with 250 mTorr, and 6 hr at 20° C. with 250 mTorr.
[d]Vacuum drying was done by placing partially stoppered vials in a desiccator and pulling a vacuum at 2–8° C.
[e]Fluidized bed drying was performed by passing nitrogen through the microspheres on a 20 μm mesh in either a fluidized bed system (see FIG. 4) or in an Amicon stirred cell where the nitrogen flow is directed upward.
[f]ND = Not determined
[g]The initial burst for this sample was assessed by measuring the cumulative release over first two days since there was significant release on days 1 and 2. There was minimal release (less than 2%) from day 2 to 10.

Table 7 provides similar data for microspheres encapsulating the adjuvant QS21. Microspheres were prepared by dissolving 3 g of PLGA (0.53 dL/g; 50:50 lactide/glycolide; MTI) in 10 mL of methylene chloride. 600 μl of QS21 (200 mg/mL in 50% ethanol) was injected into the PLGA solution while homogenizing at 15,000 rpm. After injection, the emulsion was homogenized for 1 min. This first emulsion was performed at 1° C. The first emulsion was then pumped to the inlet of a static mixer at 5 mL/min while a 9% PVA solution containing 10% ethyl acetate (3° C.) was pumped to the same inlet at 1.5 L/min. The outlet of the static mixer was attached to a stirred tank (hardening bath) containing 12 L of prefiltered water. After one hour in the hardening bath, the microspheres were filtered with a 150-μm mesh and then diafiltered with a 20-μm mesh and 30 L of 0.1% Tween at $2_{-8}$° C. The final microspheres were then dried as indicated in the Table.

TABLE 7

Effect of Drying Method on Initial Burst from Q21-PLGA Microspheres Prepared by the Water-in-Oil-in-Water Double Emulsion Method

| Core Loading | Initial Burst from Drying Method[a] (% of Total) | | |
|---|---|---|---|
| (% w/w) | Wet[b] | Lyo.[c] | Fluidized Bed[d] |
| 2.3 | 0.6 | 15 | 2 |

[a]Microspheres were incubated in release media for 1 hour and the amount of QS21 released was measured (% release = 100% * (mass QS21 release/total mass in microspheres)).
[b]Microspheres were analyzed immediately after production without drying.
[c]Lyophilization was performed with the following cycle: 4.75 hr at −55° C., 12 hr at 20° C. with 250 mTorr, and 6 hr at 20° C. with 250 mTorr.
[d]Fluidized bed drying was performed by passing nitrogen through the microspheres on a 20 μm mesh in either a fluidized bed system (see FIG. 4) or in an Amicon shirred cell where the nitrogen flow is directed upward.

We claim:

1. A method for preparing microspheres wherein an active agent is dispersed within a polymer matrix by a water-in-oil or a solid-in-oil process comprising
   (a) dissolving a polymer in an organic solvent to produce a solution;
   (b) adding an active agent or an aqueous solution thereof to the solution of step (a) to produce a polymer-active agent solid-in-oil or water-in-oil first emulsion or suspension;
   (c) extracting the excess organic solvent from the first emulsion or suspension with an aqueous solution to produce microspheres;
   (d) removing the aqueous solution sufficient to provide a final product with less than 20% residual moisture by drying the microspheres of step (c) in a fluidized bed; and (e) recovering the microspheres.

2. The method of claim 1 wherein the organic solvent is methylene chloride.

3. The method of claim 1 wherein the organic solvent is ethyl acetate.

4. The method of claim 1 wherein the organic solvent is a mixture of ethyl acetate and benzyl alcohol or acetone.

5. The method of claim 1 wherein the aqueous solution of part (c) contains polyvinyl alcohol.

6. The method of claim 5 wherein the polyvinyl alcohol solution contains ethyl acetate.

7. The method of claim 1 wherein the active agent is a dry solid.

8. The method of claim 1 wherein an aqueous solution of an active agent is added to the solution of part (a).

9. The method of claim 1 wherein the active agent is an antigen.

10. The method of claim 1 wherein the active agent is an adjuvant.

11. The method of claim 1 wherein the fluidized bed comprises a system wherein a dry gas is passed across wet microspheres.

12. The method of claim 1 wherein the polymer is a polyester.

13. The method of claim 12 wherein the polyester is poly(D-L-lactide-co-glycolide).

14. The method of claim 1 wherein the active agent is a polypeptide.

15. The method of claim 14 wherein the polypeptide is human growth hormone.

16. The method of claim 14 wherein the polypeptide is gp120.

17. A composition comprising microspheres encapsulating an active agent produced by the process of claim 1.

18. The composition of claim 17 wherein the active agent is a dry solid.

19. The composition of claim 17 wherein an aqueous solution of an active agent is added to the solution of part (a).

20. The composition of claim 17 wherein the active agent is an antigen.

21. The composition of claim 17 wherein the active agent is an adjuvant.

22. The composition of claim 17 wherein the active agent is a polypeptide.

23. The composition of claim 22 wherein the polypeptide is growth hormone.

24. The composition of claim 22 wherein the polypeptide is gp120.

* * * * *